US012741988B2

(12) United States Patent
Xia et al.

(10) Patent No.: US 12,741,988 B2
(45) Date of Patent: Sep. 22, 2026

(54) METHOD FOR TREATMENT OF DRY EYE COMPRISING APPLYING P55PIK INHIBITOR

(71) Applicant: Wuhan Yicheng Biological Technology Co., Ltd., Wuhan (CN)

(72) Inventors: Xianmin Xia, Wuhan (CN); Chaoxing Li, Wuhan (CN)

(73) Assignee: HAN YICHENG BIOLOGICAL TECHNOLOGY CO, LTD., Wuhan (CN)

( * ) Notice: Subject to any disclaimer, the term of this patent is extended or adjusted under 35 U.S.C. 154(b) by 688 days.

(21) Appl. No.: 18/312,574

(22) Filed: May 4, 2023

(65) Prior Publication Data

US 2023/0348538 A1 Nov. 2, 2023

Related U.S. Application Data

(63) Continuation-in-part of application No. PCT/CN2021/126635, filed on Oct. 27, 2021.

(30) Foreign Application Priority Data

Nov. 4, 2020 (CN) ........................ 202011215031.0

(51) Int. Cl.

| | |
|---|---|
| ***C07K 7/00*** | (2006.01) |
| ***A61K 47/66*** | (2017.01) |
| ***A61P 27/02*** | (2006.01) |
| ***C07K 7/08*** | (2006.01) |

(52) U.S. Cl.

CPC ................ *C07K 7/08* (2013.01); *A61K 47/66* (2017.08); *A61P 27/02* (2018.01)

(58) Field of Classification Search

CPC ........ C07K 7/08; A61K 47/66; A61K 9/0048; A61K 38/10; A61P 27/02

See application file for complete search history.

(56) References Cited

PUBLICATIONS

Baudouin et al. Acta Ophthalmologica. (2018). vol. 96, p. 111-119.*

Zhu et al. Experimental Eye Research. (2020). vol. 199, 108180, p. 1-9.*

* cited by examiner

*Primary Examiner* — Jeanette M Lieb

(74) *Attorney, Agent, or Firm* — MATTHIAS SCHOLL P.C.; Matthias Scholl

(57) ABSTRACT

The disclosure provides a method for treatment of dry eye. The method includes administering a patient in need thereof a P55PIK inhibitor. Also provided is a therapeutic drug for dry eye including a P55PTK inhibitor. The dry eye therapeutic drug is easy to use and has a reliable therapeutic effect.

10 Claims, 5 Drawing Sheets

Specification includes a Sequence Listing.

Treatment
0 days

Treatment
for 4 days

Treatment
for 7 days

Left eye Right eye

Left eye Right eye

Left eye Right eye

Left eye Right eye

SEQUENCE LISTING

```
Sequence total quantity: 7
SEQ ID NO: 1            moltype = AA  length = 16
FEATURE                 Location/Qualifiers
source                  1..16
                        mol_type = protein
                        organism = synthetic construct
SEQUENCE: 1
MMPYSTELIF YIEMDP                                                   16

SEQ ID NO: 2            moltype = AA  length = 27
FEATURE                 Location/Qualifiers
source                  1..27
                        mol_type = protein
                        organism = synthetic construct
SEQUENCE: 2
YGRKKRRQRR RMMPYSTELI FYIEMDP                                       27

SEQ ID NO: 3            moltype = DNA  length = 17
FEATURE                 Location/Qualifiers
source                  1..17
                        mol_type = other DNA
                        organism = synthetic construct
SEQUENCE: 3
gcttggcact tgatgta                                                  17

SEQ ID NO: 4            moltype = DNA  length = 21
FEATURE                 Location/Qualifiers
source                  1..21
                        mol_type = other DNA
                        organism = synthetic construct
SEQUENCE: 4
gctgtatgaa gaagaatata c                                             21

SEQ ID NO: 5            moltype = DNA  length = 20
FEATURE                 Location/Qualifiers
source                  1..20
                        mol_type = other DNA
                        organism = synthetic construct
SEQUENCE: 5
ggaccaggtt gtctcctgtg                                               20

SEQ ID NO: 6            moltype = DNA  length = 19
FEATURE                 Location/Qualifiers
source                  1..19
                        mol_type = other DNA
                        organism = synthetic construct
SEQUENCE: 6
tgtaggccat gaggtccac                                                19

SEQ ID NO: 7            moltype = AA  length = 16
FEATURE                 Location/Qualifiers
source                  1..16
                        mol_type = protein
                        organism = synthetic construct
SEQUENCE: 7
MMPYSTELIF YIEMDP                                                   16
```

METHOD FOR TREATMENT OF DRY EYE COMPRISING APPLYING P55PIK INHIBITOR

CROSS-REFERENCE TO RELATED APPLICATIONS

This application is a continuation-in-part of International Patent Application No. PCT/CN2021/126635 with an international filing date of Oct. 27, 2021, designating the United States, now pending, and further claims foreign priority benefits to Chinese Patent Application No. 202011215031.0 filed Nov. 4, 2020. The contents of all of the aforementioned applications, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, MA 02142.

INCORPORATION-BY-REFERENCE OF SEQUENCE LISTING

This application contains a sequence listing, which has been submitted electronically in XML file and is incorporated herein by reference in its entirety. The XML file, created on Nov. 11, 2025, is named WHZC-01201-UUS_SEQ_new.xml, and is 7,239 bytes in size.

BACKGROUND

The disclosure relates to the field of biopharmaceuticals, and more specifically, to a method for treatment of dry eye comprising applying a P55PIK inhibitor.

Dry eye is a disease associated with tear film instability and/or ocular surface damage caused by abnormalities in the quantity or quality or fluid dynamics of tears. Symptoms of dry eye include a sensation of dryness, foreign body sensation, burning, tingling, itching, photophobia, redness, blurred vision, and visual fluctuations.

Dry eye (keratoconjunctivitis sicca) can be classified based on structure and function of the tear film on the ocular surface. There are five types of dry eye: (1) aqueous-deficient dry eye, which is caused by insufficient production and/or abnormal quality of aqueous tears, such as Sjögren's syndrome and many systemic factors; (2) evaporative dry eye, which is a disease caused by abnormal lipid layer due to meibomian gland dysfunction, lid margin inflammation, use of video display terminals, eyelid defects or abnormal increased evaporation; (3) mucin-deficient dry eye, which is caused by damage to the ocular surface epithelial cells, such as drug toxicity, chemical injury, thermal burn damage to the ocular surface, and dysfunction of the corneal margin; (4) dry eye associated with abnormal tear dynamics, which is caused by abnormalities in tear film dynamics, such as abnormal blinking, delayed tear drainage, and conjunctival relaxation; (5) mixed type dry eye, which is the most common type of dry eye clinically and is caused by two or more of the above reasons.

Conventional treatments for dry eye include use of artificial tears, lubricating ointments, immunosuppressive agents, and other therapies. Some cases may require autologous serum or surgical treatment.

SUMMARY

To solve the above shortcomings or for the improvement needs of the existing technology, the disclosure provides the use of a P55PIK inhibitor for preparation of a therapeutic drug for dry eye, with the aim of providing a dry eye therapeutic drug that is easy to use and has a reliable therapeutic effect, thereby solving the technical problem that conventional dry eye therapeutic drugs can only alleviate or suppress symptoms, or are difficult to prepare.

To achieve the above objectives, the disclosure provides a method for treatment of dry eye comprising administering a patient in need thereof a P55PIK inhibitor.

In a class of this embodiment, the P55PIK inhibitor is a composition comprising a P55PIK peptide inhibitor.

In a class of this embodiment, the composition further comprises a cell-penetrating carrier or cell-penetrating adjuvant.

In a class of this embodiment, the cell-penetrating carrier is a cell-penetrating peptide or a liposome.

In a class of this embodiment, the P55PIK inhibitor comprises a peptide segment with an amino acid sequence: Met-Met-Pro-Tyr-Ser-Thr-Glu-Leu-Ile-Phe-Tyr-Ile-Glu-Met-Asp-Pro (SEQ ID NO: 7).

In a class of this embodiment, the P55PIK inhibitor comprises a cell-penetrating peptide linked to the peptide segment through a peptide bond.

In a class of this embodiment, the dry eye is moderate or severe evaporative dry eye or is associated with abnormal tear dynamics.

The second objective of the disclosure is to provide a therapeutic drug comprising the P55PIK inhibitor for dry eye.

In a class of this embodiment, the therapeutic drug for dry eye comprises at least 0.01% by weight of the P55PIK inhibitor.

In a class of this embodiment, the therapeutic drug for dry eye comprises a cell-penetrating carrier or a cell-penetrating adjuvant.

The following advantages area associated with the therapeutic drug for dry eye of the disclosure:

The disclosure provides the therapeutic drug comprising the P55PIK inhibitor for dry eye that effectively and safely treats dry eye, and the P55PIK inhibitor is a promising innovative drug with controllable quality.

DETAILED DESCRIPTION

Figure 1:
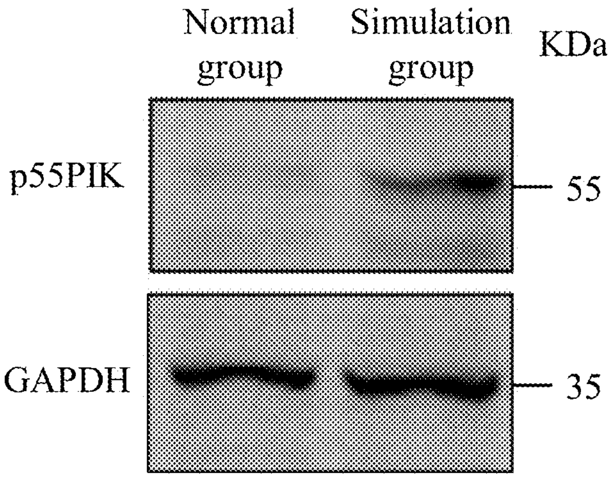
FIG. 1 is the protein electrophoresis showing the expression level of p55PIK protein in normal control group and model group of dry eye rats with low tear secretion according to Example 1 of the disclosure.

To further illustrate the disclosure, embodiments detailing a P55PIK inhibitor and a therapeutic drug comprising the P55PIK inhibitor for dry eye are described below. It should be noted that the following embodiments are intended to describe and not to limit the disclosure.

The disclosure provides a therapeutic drug for dry eye comprising a P55PIK inhibitor, with a preferred content of ≥0.01 wt. %.

Conventional P55PIK inhibitors are peptide-based preparations, such as N16 peptide comprising a sequence shown in SEQ ID NO: 1. However, the peptide-based preparations are difficult to penetrate through the biological membranes. The therapeutic drug for dry eye is formulated, for example, as ophthalmic drops, for direct application to the eye. The ophthalmic drops improve the biological activity of the P55PIK inhibitor by enhancing its penetration through membranes.

The penetration of the P55PIK inhibitor is accomplished by loading the P55PIK inhibitor onto cell-penetrating carriers or by directly using cell-penetrating artificial peptides that possesses an inhibitory activity against P55PIK. For example, the cell-penetrating artificial peptide is a TAT-N16 peptide comprising a sequence shown in SEQ ID NO: 2; the TAT-N16 peptide is constructed by linking the peptide N16 to a TAT sequence.

Based on sequences and lipid-binding ability, the cell-penetrating peptides are divided into three classes: (1) amphipathic peptides, such as transportan or TP10, generally comprise over 20 amino acid residues, and have both hydrophobic and hydrophilic amino acid residues arranged continuously along a main structure; (2) moderately amphipathic peptides, such as penetratin, pVEC and M918, have fewer amino acid residues than the amphipathic peptides; the moderately amphipathic peptides exhibit amphipathic properties when interacting with membranes, resulting in α-helical or β-folded structures; (3) non-amphipathic peptides, such as R9 and TAT, which are typically shorter than the moderately amphipathic peptides, and possess a high proportion of positively charged amino acids, like arginine.

The cell-penetrating carriers comprises liposome for encapsulation.

The efficacy of the TAT-N16 peptide (shown in SEQ ID NO: 2) is demonstrated in a rat model of dry eye, exhibiting promising results in prolonging the tear film break-up time and repairing corneal damage, particularly in cases of moderate or severe evaporative dry eye and dry eye with abnormal tear dynamics.

Additionally, membrane permeable preparations, in which the P55PIK inhibitors and cell-penetrating adjuvants are loaded onto the cell-penetrating carriers, have shown similar inhibitory effects as the rat model of dry eye and is suitable for use in treating dry eye.

Research has found that the rat model of dry eye exhibits abnormal increase in the expression of P55PIK protein, and the P55PIK inhibitor has the potential to repair corneal damage and prolong the tear film break-up time.

Example 1

TAT-N16 peptide alleviates dry eye symptoms in laboratory rats by reducing the expression level of p55PIK protein in rat eye tissues.

1 Materials and Methods 1.1 Animals, Reagents and Tools

Animals: forty-two SPF-grade healthy SD rats (150-300 g, equal numbers of male and female) were selected; both eyes of the SD rats were treated with 0.25% chloramphenicol eye drops (0.05 mL/eye/time) five times a day; before the experiment, all laboratory rats underwent an external eye examination with a slit lamp and were found to have no abnormalities, and thus were included in the study.

Reagent: 0.4% oxybucaine hydrochloride eye drops, 0.5% lidocaine hydrochloride injection. 0.25% chloramphenicol eye drops, 1% benzalkonium bromide solution, 0.5% sodium carboxymethyl-cellulose eye drops, 0.2% carbomer eye drops, 0.9% NaCl injection, 0.5 mg/mL atropine injection, and 2% sodium fluorescein solution.

Tools: Schirmer tear test strips, a slit lamp, a 5 mL sterile syringe, a 5-gauge needles, forceps, a needle holder, ophthalmic scissors, a stopwatch, a suture needle, No. 1 black silk thread, P55PIK antibody (CST), GAPDH (ABclonal), TRizol kit, and a real-time quantitative PCR master mix.

1.2 Modeling and Grouping 1.2.1 Modeling: a rat model of dry eye induced by corneal epithelial injury, was prepared by removing the lacrimal glands and adding benzalkonium bromide solution dropwise; eighteen laboratory rats (an equal number of male and female) were selected at random; the hair surrounding the eyes was shaved and disinfected; the surface anesthesia was achieved with 0.4% oxybucaine; the eighteen laboratory rats were anesthetized with 1 mL of 0.5% lidocaine injected into the eyes; a small incision was made in the skin in front of the ear of the eighteen laboratory rats; the lacrimal glands on both sides were peeled off and removed; 1% benzalkonium bromide solution was dropped into the eyes; and the cornea was observed on the second day.

Grouping and administration: the eighteen rats were then randomly divided into three groups, with 6 laboratory rats in each group (male and female in equal numbers); Group 1 was the blank control group and received no treatment; Group 2 was the solvent control group and was treated with solvent eye drops that contained a solvent but no TAT-N16 peptide; Group 3 was the drug treatment group and was treated with eye drops comprising 0.1% TAT-N16 peptide; the eye drops were administered four times a day (1 drop/time) for 7 days; the corneal epithelial injury was evaluated on days 0, 4 and 7 after treatment.

Detection method and scoring criteria: corneal staining was performed by injecting 1 drop pf sodium fluorescein into the conjunctival sac using the 5 mL sterile syringe with the 5-gauge needle; the corneal epithelium was observed under the blue light from the slit lamp after 5 minutes; and the scoring criteria were shown in Table 1.

1.2.2 Modeling: a rat model of dry eye caused by low tear secretion, was established using the Burgalassi method of atropine injection into the lacrimal glands; eighteen laboratory rats, with equal numbers of male and female, were given 0.4% oxybucaine hydrochloride eye drops in both eyes and injected with 0.25 mL of 0.5 mg/mL atropine into the lacrimal glands four times a day for both eyes; the results of lacrimal secretion test were recorded 0.5 hours after the atropine injection every day; and the atropine injection was continued until the 7th day.

Grouping and administration: six laboratory rats, with equal numbers of male and female, were used as the normal control group and were not modeled; the eighteen successfully modeled laboratory rats were randomly divided into three model groups, with 6 rats in each model group, half male and half female; Model group 1 was the blank control group and received no treatment; Model group 2 was the solvent control group and treated with solvent eye drops that contained a solvent but no TAT-N16 peptide; Model group 3 was the drug treatment group and was treated with eye drops comprising 0.1% TAT-N16 peptide; the eye drops was administered four times a day (1 drop/time) for 7 days; the amount of the lacrimal secretion of each eye was recorded on days 0, 4 and 7 after treatment; the expression levels of P55PIK gene and p55PIK protein in the rat eyes of the normal control group and the model groups were detected.

1.2.2.1 Lacrimal secretion test (Schirmer's test II): due to the smaller eyeballs of SD rats compared to human, the Schirmer tear test strips designed for human use were not suitable for use in the SD rats; therefore, the Schirmer's test II was conducted by cutting a 5 mm×35 mm Schirmer tear test strip into two strips of 2.5 mm×35 mm each, folding the front end, and lightly placing the Schirmer tear test strip at the junction of the posterior-middle ⅓ of the lower eyelid; after 5 minutes, the Schirmer tear test strips were removed; and the length of the Schirmer tear test strips wetted by tears were measured for 2 minutes and the measurement was repeated three times to obtain an average value; the results were recorded before the treatment, and on the 4th and 7th day after treatment.

1.2.2.2 Western Blotting

1. Sample Preparation

1) The rat eyes were processed, washed 2-3 times with PBS; and then 50-100 uL of denaturing lysis buffer comprising a protease inhibitor was added;

2) the protein was collected by ultrasonic crushing the sample; specifically, the sample was placed in an EP tub; the EP tube was then inserted into the ice and put on an ultrasonic crusher to ultrasound for 5 s and pause for 10 s, with a sonicate power of 45% for 5 cycles;

3) the EP tube comprising the crushed sample was centrifuged at 12,000 rpm for 10 minutes at 4° C.; the cell debris and impurities were removed; and the supernatant was collected;

4) the concentration of proteins in the supernatant was measured on Nanodrop;

5) 25 μL of 5× protein loading buffer was added in proportion, mixed thoroughly; the protein was denatured in a metal bath for 10 min to prepare the sample.

The 5× protein loading buffer was prepared as follows:

| | | |
|---|---|---|
| Tris•HCl (pH 6.8) | 250 mM | 3.0285 g |
| SDS | 10% | 10 g |
| Bromophenol blue | 0.50% | 0.5 g |
| Glycerin | 50% | 50 mL |
| DTT (Dithiothreitol) | 500 mM | 7.7250 g |
| Water | | to 100 mL |

2. SDS-PAGE Gel Electrophoresis

SDS-PAGE gel was prepared; the protein volume loaded on the SDS-PAGE gel was calculated based on the determined protein concentration; 10-20 g of the protein was loaded into each well; the electrophoresis was conducted at a constant voltage, starting with 80 V voltage and then switching to 120 V when the sample enters the separating gel; and the electrophoresis was stopped when bromophenol blue run off the separating gel.

3. Wet Transfer to PVDF Membrane

For the wet transfer to a PVDF membrane, a transfer buffer was prepared; after the electrophoresis was completed, the SDS-PAGE gel was peeled off, and the stacking gel was removed; the separating gel was put in the transfer buffer; the transfer was carried out by plugging positive and negative electrodes into the respective outlets, takin care to avoid transfer membrane displacement caused by the shifting between the interlayers; the transfer tank was placed in an icebox to cool down; and the transfer was completed at a constant current of 200 mA for 1.5-2 h.

4. Immunostaining

After wet transfer, the PVDF membrane was blocked with skimmed milk powder, incubated with a primary antibody for 2 h at room temperature or overnight at 4° C.; the PVDF membrane was washed and subsequently incubated with a secondary antibody on a shaker for 1 h at room temperature, ensuring the secondary antibody was protected from light exposure during incubation; the PVDF membrane was washed again and scanned on an Odyssey two-color infrared imaging system; specifically, the intensity of a laser produced by the Odyssey two-color infrared imaging system was adjusted; the signals from the proteins binding to the PVDF membrane was scanned based on the species of the secondary antibody.

1.2.2.3 Detection of Gene Expression by Real-Time Fluorescent Quantitative PCR

1. Extraction of Total RNA from the Eyes

Total RNA was extracted using the TRizol kit following the manufacturer's instructions; the concentration of the total RNA was measured using a UV spectrophotometer, with a 260/280 ratio of 1.87-1.98;

the primer sequences for p55PIK gene were as follows:

```
p55PIK-F:
                                      (SEQ ID NO: 3)
5'-GCTTGGCACTTGATGTA-3';
and

p55PIK-R:
                                      (SEQ ID NO: 4)
5'-GCTGTATGAAGAAGAATATAC-3';
```

the primer sequences for the internal reference gene GAPDH were as follows:

```
GAPDH-F:
                                      (SEQ ID NO: 5)
5'-GGACCAGGTTGTCTCCTGTG-3';
and

GAPDH-R:
                                      (SEQ ID NO: 6)
5'-TGTAGGCCATGAGGTCCAC-3'.
```

2. Reverse Transcriptase PCR

Reverse transcriptase PCR was performed using TransScript® One-step gDNA Removal and cDNA Synthesis SuperMix (TransGen Biotech, Beijing, China);

1) the PCR reaction components were added, mixed gently, and placed in CFX96 qPCR instrument under the following conditions:

| Cycle | Step | Temperature | Time | Readout |
|---|---|---|---|---|
| 1 | Initial denaturation | 95° C. | 10 min | No |
| | Denaturation | 95° C. | 30 sec | No |
| 40 | Annealing | 55° C. | 15 sec | No |
| | Elongation | 72° C. | 15 sec | Yes |

Melting Curve

| Temperature | Increment | Time | Readout |
|---|---|---|---|
| 65-95° C. | 0.5° C. | 5 sec/each | Yes |
| 30° C. | | 30 sec | No |

Data was analyzed using the ΔΔCt method.

2. Results 2.1 Rat Model of Dry Eye Induced by Corneal Epithelial Injury

Figure 3:
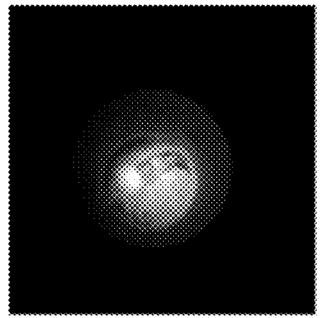
FIG. 3 is the sodium fluorescein staining of the cornea in dry eye rats with corneal epithelial damage that were treated with 0.1% TAT-N16 peptide according to Example 1 of the disclosure.
Figure 3:
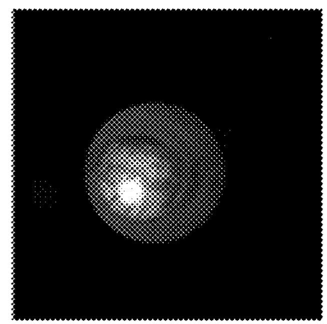
Figure 3:
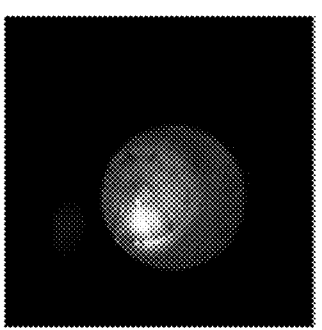

Before treatment, no statistically significant difference ($P>0.05$) in corneal epithelial injury score was observed among groups. Following 4 days of treatment, no statistically significant difference ($P>0.05$) in corneal epithelial injury score was found between the drug treatment group and the blank control group or between the drug treatment group and the solvent control group. However, after 7 days of treatment, the corneal epithelial injury score in the drug treatment group was significantly lower ($P<0.05$) than that in the blank control group or the solvent control group (shown in Table 2). The corneal stained by sodium fluorescein was observed and compared (FIG. 3).

2.2 Rat Model of Dry Eye Induced by Decreased Tear Secretion

The tear secretion of laboratory rats decreased significantly ($P<0.001$) from (8.98±1.36) mm to (3.21±1.24) mm after modeling, indicating successful modeling. Furthermore, no statistically significant difference ($P>0.05$) in tear secretion was found among groups before and after modeling, indicating comparability of tear secretion among groups. On the 4th and 7th day of treatment, the tear secretion in the drug treatment group was significantly higher ($P<0.05$) than that in the control groups (Table 3).

Western blotting was performed to measure the expression level of the p55PIK protein in eye tissue samples of the laboratory rats in the normal control group and the model groups with dry eye caused by decreased tear secretion. The results revealed a significant increase in the expression levels of P55PIK protein in the eyes of the model groups compared to the normal control group (FIG. 1).

Figure 2:
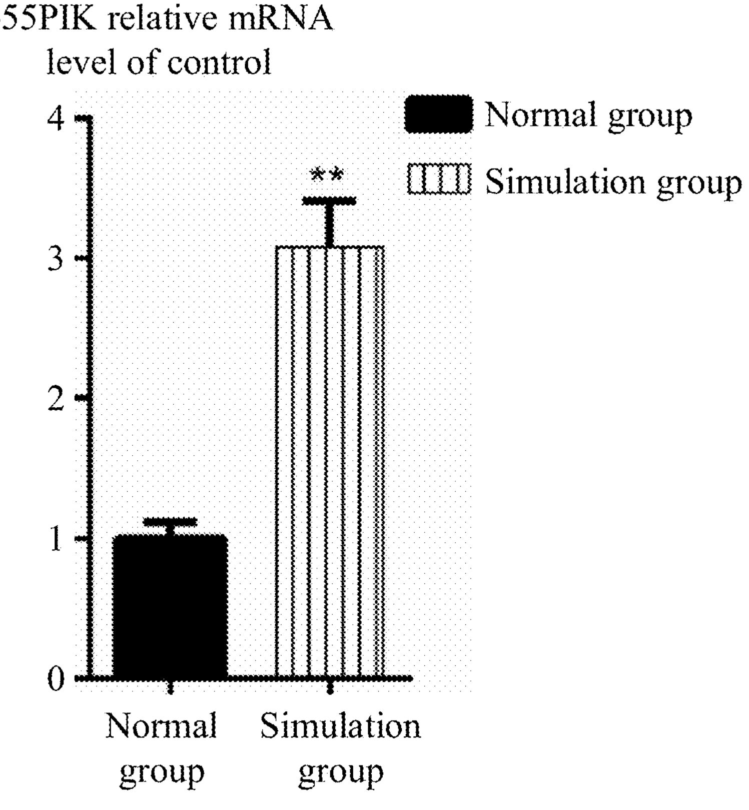
FIG. 2 is a statistical chart of the expression of p55PIK gene in normal control group and model group of dry eye rats with low tear secretion according to Example 1 of the disclosure.

Real-time quantitative PCR was employed to measure the transcription levels of the P55PIK gene in the eyes of rats with dry eye caused by decreased tear secretion. The results showed a significant upregulation of the p55PIK gene transcription in the eyes of the model groups compared to the normal control group (FIG. 2).

TABLE 1

Corneal epithelial injury scores.

| Corneal Condition | 0 | 1 | 2 | 3 | 4 |
|---|---|---|---|---|---|
| Corneal Opacity (densest part) | None | Diffuse opacity, iris clearly visible | Semi-transparent area easily distinguishable, iris blurred | Gray-white opaque area, iris details not clear, pupil size barely visible | Cornea opaque, iris indiscernible |
| Fluorescein staining of cornea | None | Coloring but area <25% | Coloring area 25%-50% | Coloring area 50%-75% | Coloring area >70% |

TABLE 2

Comparison of corneal epithelial injury scores ($\bar{x} \pm s$, n = 6) among different groups of rats with a dry eye model

| Group | Blank control group | Solvent control group | Drug treatment group |
|---|---|---|---|
| Before treatment | 5.84 ± 1.20* | 5.35 ± 1.11* | 4.81 ± 1.61* |
| After 4 days of treatment | 4.32 ± 1.41 | 4.72 ± 1.15 | 3.08 ± 1.43 |
| After 7 days of treatment | 3.24 ± 1.19 | 3.09 ± 1.27 | 0.84 ± 0.96* |

Note:
The blank control group received no treatment. Data comparison was conducted through one-way ANOVA, and the results were compared to the blank control group, $P < 0.01$.

TABLE 3

Comparison of Schirmer's test II values ($\bar{x} \pm s$, mm, n = 6) in each group of dry eye model rats with reduced tear secretion

| Group | Normal control group | Blank control group | Solvent control group | Drug treatment group |
|---|---|---|---|---|
| Before treatment | 8.98 ± 1.26 | 3.11 ± 1.35 | 3.07 ± 0.83 | 3.29 ± 1.34 |
| After 4 days of treatment | 9.04 ± 1.17 | 3.35 ± 0.94 | 3.32 ± 0.18 | 5.74 ± 1.59 |
| After 7 days of treatment | 9.11 ± 1.09 | 4.29 ± 1.02 | 4.17 ± 0.82 | 8.58 ± 1.73* |

Note:
The normal control group consisted of non-model rats, and the blank control group received no treatment. Data comparison was conducted through one-way ANOVA, and the results were compared to the blank control group, $P < 0.05$.

Example 2

TAT-N16 peptide relieves dry eye symptoms in laboratory rats

1. Materials and Reagents 1.1 Materials and Reagents

Materials: fifty healthy male C57BL/6 mice (18-20 g) with no abnormalities in the eyes were used.

Reagents: 0.1% TAT-N16 peptide eye drops, 0.2% benzalkonium chloride solution, 1% fluorescein sodium solution, pentobarbital, phenol red thread, and regents for Periodic acid-Schiff (PAS) staining.

2. Method 2.1 Modeling

The healthy male C57BL/6 mice were kept in a controlled environment with a temperature of (25±1°) C, a relative humidity of (25±5)%, and light-dark cycles (9 AM-9 PM) with simulated dawn and dusk. Forty mice (80 eyes) were treated with 5 L of 0.2% benzalkonium chloride solution twice a day (8:00 AM and 6:00 PM) for 14 days to induce dry eye symptoms, while the remaining ten mice (20 eyes) received no treatment and served as a baseline control.

2.2 Evaluation of Dry Eye Rat Model and Drugs Screening

Modeling was carried out on the 15th day; and the dry eye rat models were screened based on tear film break-up time (BUT), fluorescein sodium staining of corneal, and Schirmer's test I for tear secretion.

Tear film break-up time (BUT) was used to assess the tear film stability: 1 L of 1% fluorescein sodium solution was instilled into the conjunctival sac of the mouse, and the mouse was held and blinked artificially three times; the upper and lower eyelids of the mouse were then separated; and the tear film was observed under cobalt blue filter on a slit lamp; the tear film break-up time was recorded as the number of seconds that elapse between the last blink and the appearance of the first dry spot in the tear film of the cornea; each eye was measured three times, and the average of the three measurements was recorded in seconds.

Fluorescein sodium staining was carried out to determine if there any epithelial damage in the corneal of mice; one drop of 1% fluorescein sodium solution was instilled into the conjunctival sac of the mouse eyes; after 1 minute, the corneal epithelial stained by fluorescein sodium was observed under the cobalt blue filter on the slit lamp.

Scoring criteria: the cornea was divided into 4 quadrants; and a scoring system was used to assess the staining; each quadrant was given a score ranging from 0 to 4 points, with a total score of 16 points. A score of 0 indicated no staining; 1 point represented less than 30 punctate staining spots; 2 points represented more than 30 punctate staining spots but not diffuse; 3 points represented obviously diffuse staining but no patchy staining; 4 points represented patchy staining.

To assess tear secretion, Schirmer's test I was performed on mice at 3 PM each day using the phenol red thread; general anesthesia was induced by intraperitoneal injection of pentobarbital (50 mg/kg body weight); the lower eyelid was grasped and gently pulled down; front end of the phenol red thread, folded 1 mm, was placed on the conjunctival surface near the outer canthus of the lower eyelid for 15 seconds; the length of the red-stained portion of the phenol red thread was measured and recorded; the eyelid was then closed after the Schirmer's test I to avoid excessive exposure; each eye was tested twice, and the average length of the red-stained portion of the phenol red thread was recorded as the final result.

To assess changes in the number of conjunctival goblet cells, paraffin sections of the conjunctival fornix was stained with PAS; the number of conjunctival goblet cells in the blank control group and the solvent control group was significantly less than that in the normal conjunctiva; after treatment with the eye drops comprising the TAT-N16 peptide, the number of conjunctival goblet cells increased significantly with statistical significance.

2.3 Grouping and Treatment of Dry Eye Model:

Thirty rat models (60 eyes) of dry eyes were selected based on the above criteria and were randomly divided into three groups: A, B, and C; each group had an equal number of males and female rats. Group A, the drug treatment group, was treated with the eye drops comprising 0.1% TAT-N16 peptide, four times a day; Group B, the solvent control group, was treated with eye drops without TAT-N16 peptide, four times a day; and Group C, the blank control group, received no treatment; on days 1, 4, and 7 after treatment, BUT, Schirmer's test I, and fluorescein sodium staining were performed; on the 7th day, the paraffin sections of the conjunctival fornix was stained by PAS stain; and the number of PAS-positive goblet cells was counted.

Figure 4:
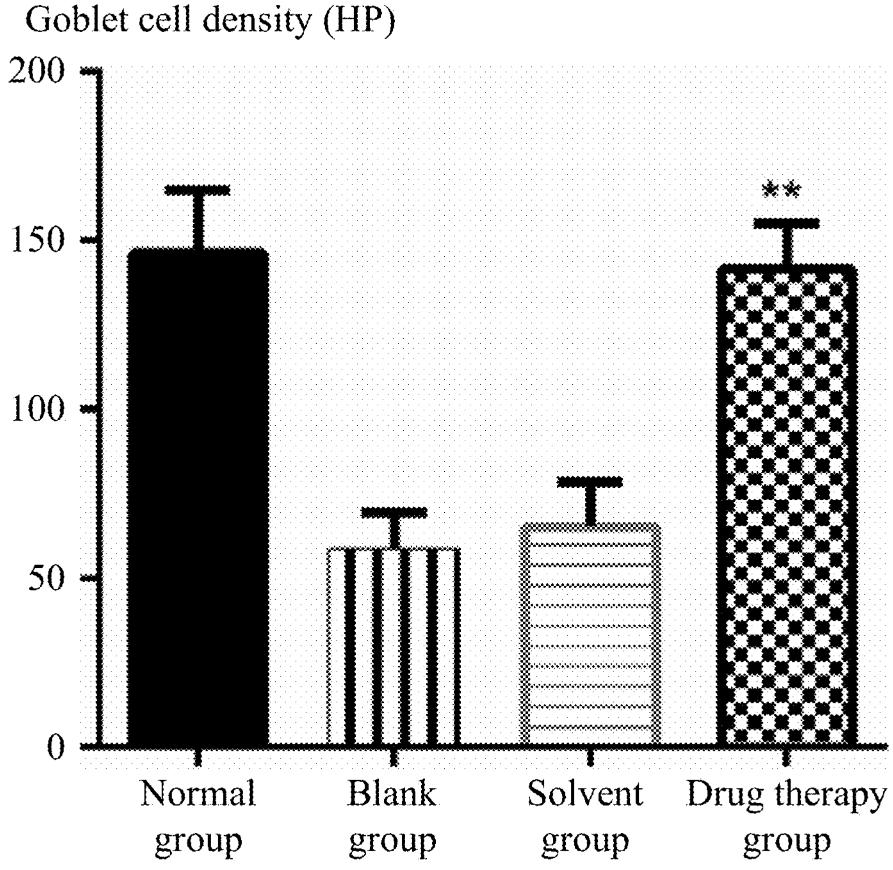
FIG. 4 shows the density of conjunctival goblet cells on the 7th day of treatment in laboratory rats according to Example 2 of the disclosure.

Results:

After inducing dry eye in rats, the rats in drug treatment group were treated with TAT-N16 peptide eye drops for 7 days, and the therapeutic effect on dry eye was observed. On the 4th day of treatment, the tear film break-up time in the drug treatment group was significantly longer than that in the blank control group, model control group, and solvent control group; the tear secretion volume was significantly higher in the drug treatment group compared to the blank control group and solvent control group; additionally, the corneal fluorescein staining score in the drug treatment group was significantly lower than that in the blank control group, model control group, and solvent control group. After 7 days of continuous treatment, the tear film break-up time in the drug treatment group was significantly longer than that in the blank control group, model control group, and solvent control group, and the difference was statistically significant (P=0.007) as shown in Table 4; moreover, the tear secretion volume in the drug treatment group was significantly higher than that in the blank control group and solvent control group, and the difference was statistically significant (P<0.05) as shown in Table 5; the corneal fluorescein staining score in the drug treatment group was significantly lower than that in the blank control group, model control group, and solvent control group, and the difference was statistically significant (P<0.05) as shown in Table 6; furthermore, the density of conjunctival goblet cells in the drug treatment group was significantly higher than that in the blank control group and solvent control group, and the difference was statistically significant (P<0.01) as shown in FIG. 4.

TABLE 4

Changes in tear film break-up time (BUT) values ($\bar{x} \pm s$) (s) within each group after drug treatment

| Group | Normal control group | Blank control group | Solvent control group | Drug treatment group |
|---|---|---|---|---|
| 0 d | 6.05 ± 0.32 | 3.65 ± 0.26 | 3.50 ± 0.46 | 3.49 ± 0.43* |
| 4 d | 5.92 ± 0.73 | 3.78 ± 0.99 | 4.55 ± 0.12 | 4.82 ± 0.57* |
| 7 d | 6.11 ± 0.19 | 4.09 ± 0.38 | 4.61 ± 0.33 | 5.99 ± 0.55** |

Note;
the BUT values in each group were compared to the blank control group,
*P < 0.05,
**P < 0.01

TABLE 5

Changes in Schirmer's test I values ($\bar{x} \pm s$, mm) within each group after drug treatment

| Group | Normal control group | Blank control group | Solvent control group | Drug treatment group |
|---|---|---|---|---|
| Before treatment | 6.18 ± 0.36 | 4.01 ± 0.33 | 4.12 ± 0.35 | 4.19 ± 0.24 |
| 4 days of treatment | 6.04 ± 0.51 | 4.15 ± 0.54 | 4.25 ± 0.44 | 5.14 ± 0.29 |
| 7 days of treatment | 6.21 ± 0.29 | 4.19 ± 0.32 | 4.28 ± 0.62 | 5.88 ± 0.63* |

Note:
The normal control group consisted of non-mode 1 rats, and the blank control group received no treatment. Data comparison was conducted through one-way ANOVA, and the results were compared to the blank control group,
*P < 0.05.

TABLE 6

Changes in corneal fluorescein staining scores ($\bar{x} \pm s$) (s) within each group after drug treatment

| Group | Normal control group | Blank control group | Solvent control group | Drug treatment group |
|---|---|---|---|---|
| 0 d | 0.14 ± 0.32 | 8.66 ± 1.06 | 8.51 ± 1.12 | 8.29 ± 1.31* |
| 4 d | 0.12 ± 0.21 | 8.72 ± 0.79 | 8.05 ± 0.82 | 4.12 ± 0.81** |
| 7 d | 0.10 ± 0.18 | 9.09 ± 1.03 | 7.61 ± 1.13 | 2.79 ± 1.25* |

Note;
the corneal fluorescein staining scores in each group were compared to the blank control group,
*P < 0.05,
**P < 0.01

Example 3

TAT-N16 peptide relieves dry eye symptoms in New Zealand rabbits

1 Materials and Method 1.1 Materials and reagents 1.1.1 Materials: thirty healthy New Zealand white rabbits of both sexes, weighing between 2.1-2.5 kg, were used for the experiment; the New Zealand white rabbits were raised in compliance with the international standards for animal experiments in ophthalmology and visual science research.

1.1.2 Reagents: 0.1% TAT-N16 peptide eye drops, benzalkonium chloride (BAC) (Sigma) diluted to a concentration of 0.1% in deionized water, Schirmer tear test strips, fluorescein sodium ophthalmic strips, nitrocellulose membranes (PALL), and periodic acid-Schiff (PAS) stain kits.

1.2 Method 1.2.1 Grouping: thirty New Zealand white rabbits were randomly divided into three groups, each comprising 10 rabbits: a blank control group, a solvent control group, and a drug treatment group.

1.2.2 Preparation of a rabbit model of dry eye: the right eye of each rabbit was used to establish a dry eye rabbit model by administering 0.1% benzalkonium chloride eye drops twice a day for 4 weeks. After 4 weeks, the dry eye rabbit model was evaluated, with the conjunctiva appearing dry, tear production being reduced, and Schirmer test values being less than 10 mm/5 min (compared to the control group, where all Schirmer test values were above 10 mm). The tear film break-up time (BUT) was less than 10 s; and fluorescein staining revealed point or patch staining on the conjunctiva, indicating the successful establishment of the rabbit model of dry eye.

1.2.3 Drug preparation and usage: a liquid formulation of 0.1% TAT-N16 peptide eye drops were prepared by dissolving the peptide raw materials in physiological saline according to a weight ratio of 0.1%. The eye drops comprising 0.1% TAT-N16 peptide were administered 2 drops, 3 times a day for 7 days. The blank control group received no treatment, and the solvent control group received physiological saline eye drops 2 drops, 3 times a day for 7 days. The normal eye group served as a normal control group.

1.3 Specimen collection and animal testing were conducted by the same individual. The examination time, location, illumination brightness, and temperature were consistent throughout the experiment. The rabbit conjunctiva appearance, fluorescein staining, tear film break-up time were analyzed using a slit lamp before and on days 4 and 7 after treatment; additionally, the Schirmer's test and conjunctival impression cytology (CIC) were carried out.

1.3.1 Schirmer's test: the corneal surface was anesthetized with oxybuprocaine hydrochloride; a cotton swab was used to absorb the fluid around the eyelid; the Schirmer tear test strips were placed at the junction of the ⅓ posterior-middle of the lower conjunctival sac of the New Zealand white rabbit, with the remaining part hanging on the skin surface; the New Zealand white rabbit was then instructed to close its eyes, and after 5 minutes, the length of wet portion of the Schirmer tear test strips was measured.

1.3.2 Tear film break-up time test: the fluorescein sodium ophthalmic strips were placed on the lower conjunctival sac for a moment, so that the fluorescein sodium was evenly distributed on the ocular surface; the eyelid was maintained open and observed under cobalt blue filter on a slit lamp; the tear film break-up time was recorded as the number of seconds that elapse between the last blink and the appearance of the first dry spot in the tear film of the cornea; The time from the opening of the eyelid to the appearance of the first dry spot on the tear film was recorded under a slit lamp microscope with cobalt blue light; each eye was measured three times, and the average of the three measurements was recorded in seconds.

1.3.3 Conjunctival impression cytology (CIC) examination: CIC examination was performed on days 1, 4, and 7 after treatment; the nitrocellulose membranes were cut into two strips of 3.5 mm×3.5 mm each, soaked in distilled water for 4 h, and then dried; after surface anesthesia, the rough side of the two strips of the nitrocellulose membranes were placed on the nasal and temporal quadrants of the conjunctiva and pressed for 10 seconds to obtain surface epithelial cells; the nitrocellulose membranes were then fixed in 95% ethanol and stained with periodic acid-Schiff (PAS); the number of the goblet cells was counted under an optical microscope and graded according to the Nelson scoring system.

2 Results 2.1 Before treatment, Schirmer's test values for the rabbit model of dry eye were all below 10 mm; there were no significant differences in Schirmer's test values among the blank control group, solvent control group, and drug treatment group, which measured (8.41±0.69) mm, (8.50±0.23) mm, and (8.38±0.57) mm, respectively. However, on the 4th day of treatment, the Schirmer test value of the drug treatment group was significantly increased to (12.02±1.21) mm compared to before treatment, as well as compared to the blank control group and solvent control group. On the 7th day of treatment, the Schirmer's test value of the drug treatment group was significantly increased to (16.31±1.45) mm compared to before treatment, as well as compared to the blank control group and solvent control group, as shown in Table 7.

2.2 Before treatment, the tear break-up time (BUT) was all below 10 s; there were no significant differences in BUT values among the blank control group, solvent control group, and drug treatment group, which measured (8.55±1.06) s, (8.11±0.82) s, and (8.24±1.13) s, respectively. However, on the 4th day of treatment, the BUT value of the drug treatment group was significantly increased to (11.72±1.27) s compared to before treatment, as well as compared to the blank control group and solvent control group. On the 7th day of treatment, the BUT value of the drug treatment group was significantly increased to (15.31±1.85) s compared to before treatment, as well as compared to the blank control group and solvent control group, as shown in Table 8.

2.3 After preparation of a dry eye model stained with the fluorescein sodium, the rabbit conjunctiva appeared dry and lackluster to the naked eye, with dot-like and patchy staining visible. However, after 4 days of treatment, the appearance of the rabbit conjunctiva improved, tear production increased, and the dot-like and patchy staining on the conjunctiva decreased. After 7 days of treatment, the conjunctiva appeared moist, tear production significantly increased, and no staining was observed on the conjunctiva.

Figure 5:
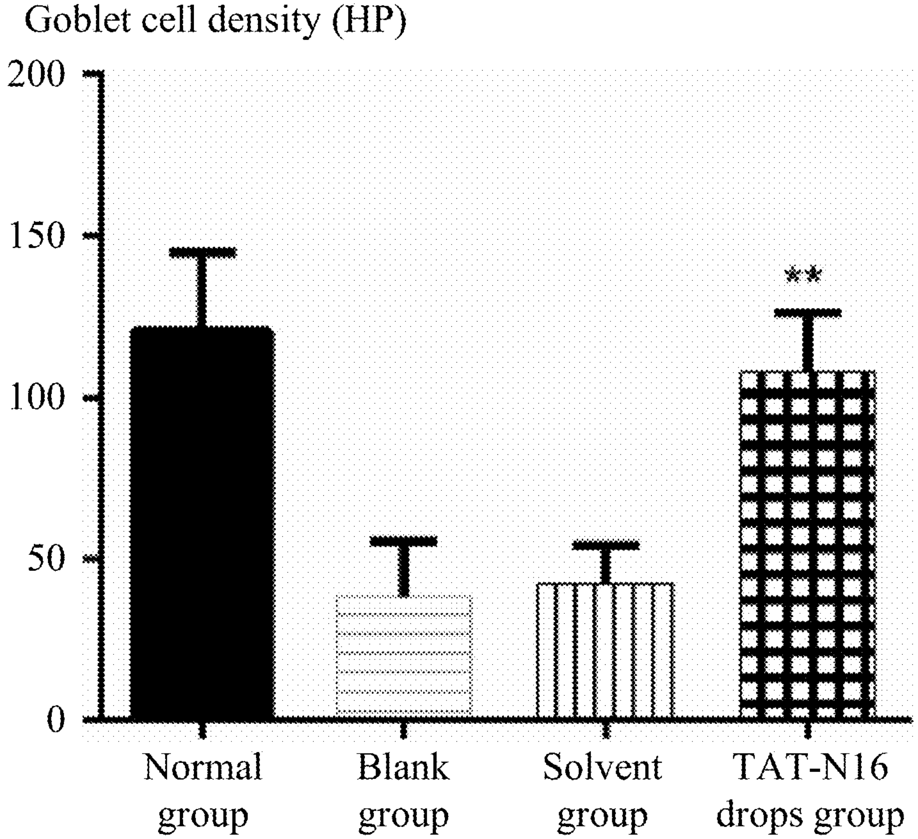
FIG. 5 shows the density of conjunctival goblet cells on the 7th day of treatment in New Zealand rabbits according to Example 3 of the disclosure.

2.4 There was a statistically significant difference in goblet cell density observed during the CIC examination between the model control group and the normal control group. Following medication, the drug treatment group showed a gradual increase in the goblet cell density, which was statistically significant when compared to before medication, as demonstrated in FIG. 5.

TABLE 7

Changes in Schirmer' test values (mm) within each group after drug treatment

| Group | Normal control group | Blank control group | Solvent control group | Drug treatment group |
|---|---|---|---|---|
| 0 d | 16.78 ± 1.09* | 8.41 ± 0.69 | 8.50 ± 0.23 | 8.38 ± 0.57* |
| 4 d | 17.02 ± 1.21** | 8.71 ± 0.91 | 8.61 ± 0.25 | 12.02 ± 1.21** |
| 7 d | 17.31 ± 1.35** | 8.55 ± 0.78 | 8.25 ± 0.91 | 16.31 ± 1.45** |

Note;
the Schirmer' test values in each group were compared to the blank control group,
*P < 0.05,
**P < 0.01

TABLE 8

Changes in tear film break-up time (BUT) values (s) within each group after drug treatment

| Group | Normal control group | Blank control group | Solvent control group | Drug treatment group |
|---|---|---|---|---|
| 0 d | 16.05 ± 1.12* | 8.55 ± 1.06 | 8.11 ± 0.82 | 8.24 ± 1.13* |
| 4 d | 15.92 ± 1.33* | 8.27 ± 0.99 | 8.30 ± 0.57 | 11.72 ± 1.27** |
| 7 d | 16.11 ± 1.19** | 8.59 ± 1.28 | 8.54 ± 1.19 | 15.31 ± 1.85** |

Note;
the BUT values in each group were compared to the blank control group,
*P < 0.05,
**P < 0.01

Example 4

Population Experiment

Currently, volunteers have been recruited to test the dry eye therapeutic effect of the 0.1% TAT-N16 peptide eye drops disclosed by the disclosure. The aim of the population experiment is to further demonstrate the effectiveness of the 0.1% TAT-N16 peptide eye drops in treating dry eye syndrome.

Figure 6A:
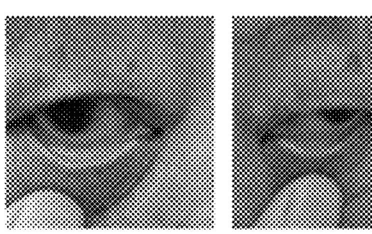
FIGS. 6A-6D show the photographic record of the cases according to Example 4 of the disclosure.
Figure 6A:
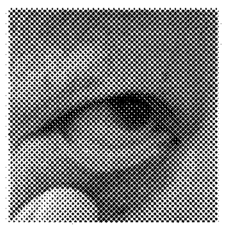
Figure 6A:

Case 1: Ms. Wu, a 70-year-old female, had been suffering from dry eyes, itching, foreign body sensation and photophobia for 3 years, and was diagnosed with dry eye syndrome. Although she frequently used artificial tears, but they only provided short-term relief and had limited efficacy. However, after using the 0.1% TAT-N16 peptide eye drops, 1-2 drops, three times a day, her dry eye symptoms improved significantly on the first day, surpassing the effect of the artificial tears. By the second day, her eyes felt moist and the symptoms of dryness, itching, and foreign body sensation were significantly relieved. On the third day, her symptoms were further reduced, and the drug effect was fast, making her eyes comfortable within 3 minutes of application, and long-lasting effects. After a week of use, the dry eye symptoms have essentially disappeared, as shown in FIG. 6A.

Figure 6B:
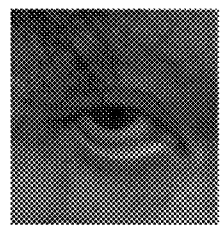
Figure 6B:
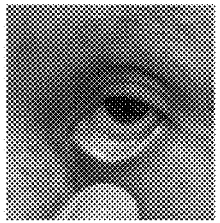
Figure 6B:
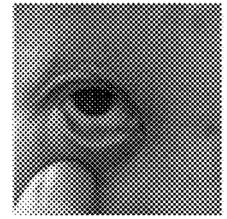
Figure 6B:
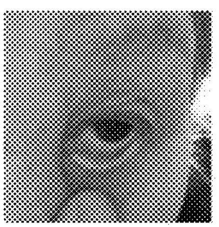

Case 2: Ms. Huang, a 63-year-old female, has been suffering from dry eyes, itching, and tearing when exposed to wind for over a year, and slight conjunctival congestion, and was diagnosed with dry eye syndrome. Despite intermittently using the artificial tears and levofloxacin eye drops in the past, her symptoms persisted. However, after using the 0.1% TAT-N16 peptide eye drops, 1-2 drops, three times a day, she experienced significantly relief from dry eye and itching on the first day, and the eye comfort improved. By the second day, the conjunctival congestion disappeared, and her eyes became moister. On the fourth day, her symptoms of tearing when exposed to wind had significantly reduced, and she continued to feel comfortable. After a week of continuous drug treatment, the conjunctival congestion has cleared up, and her dry eye symptoms has mostly disappeared, as illustrated in FIG. 6B.

Figure 6C:
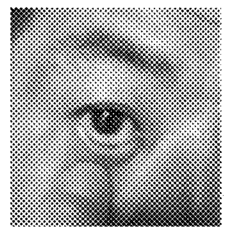
Figure 6C:
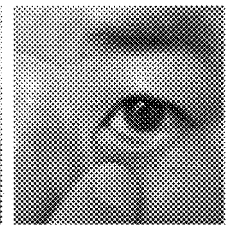
Figure 6C:
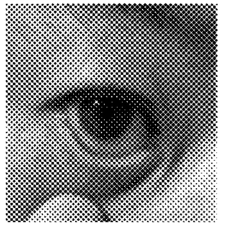
Figure 6C:
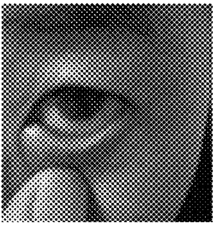

Case 3: Mr. Xu, a 35-year-old male IT worker, had been suffering from dry eyes for over a year and was diagnosed with dry eye syndrome. Although he had previously used artificial tears, for short-term relief, his symptoms persisted, and both conjunctiva remained congested. However, after using the 0.1% TAT-N16 peptide eye drops, 1-2 drops, three times a day, his eyes felt comfortable and moisturized within 5 minutes of use, and the drug effect lasted for a long time. Within three days of use, his dry eye symptoms significantly improved, and after continuous use for a week, thy disappeared completely, without any recurring dryness after discontinuation. He reported that the 0.1% TAT-N16 peptide eye drops were highly effective and shows a long-lasting effect, as shown in FIG. 6C.

Figure 6D:
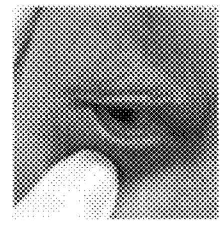
Figure 6D:
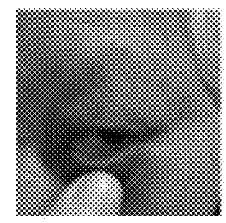
Figure 6D:
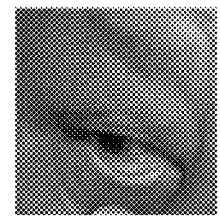
Figure 6D:
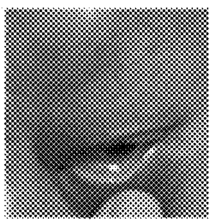

Case 4: Ms. Qing, a 67-year-old female, had been suffering from dry eyes, foreign body sensation, photophobia for two years, and slight congestion of eyelids and conjunctiva, and was diagnosed with dry eye syndrome. Previous use of eye drops of an unknown type has been unsatisfactory, and she needed glasses when going out. After using the 0.1% TAT-N16 peptide eye drops, 1-2 drops, three to five times a day, she felt comfortable within 5 minutes of use, and the photophobia was reduced. After one day, the conjunctival congestion was relieved, and she could go out without wearing glasses for a period of time. After continuous use of the disclosed eye drops for one week, the congestion of the eyelids and conjunctiva disappeared, and the symptoms of dry eyes and photophobia were largely eliminated. Currently, she rarely wears glasses when going out (unless there is discomfort in a special environment, as shown in FIG. 6D.

It will be obvious to those skilled in the art that changes and modifications may be made, and therefore, the aim in the appended claims is to cover all such changes and modifications.

What is claimed is:

1. A method for treatment of dry eye disease, the method comprising administering to a patient in need thereof a composition, wherein the composition comprises a p55PIK inhibitor, and the p55PIK inhibitor comprises:

(1) a peptide segment comprising an amino acid sequence of SEQ ID NO: 7; and (2) a cell-penetrating peptide linked to the peptide segment through a peptide bond.

2. The method of claim 1, wherein the dry eye is moderate or severe evaporative dry eye or is associated with abnormal tear dynamics.

3. The method of claim 1, wherein the p55PIK inhibitor has an amino acid sequence of SEQ ID NO: 2.

4. The method of claim 1, wherein the dry eye disease is induced by decreased tear secretion.

5. The method of claim 1, wherein the composition comprises at least 0.01 wt. % of the p55PIK inhibitor.

6. The method of claim 1, wherein the composition comprises a saline solution of the p55PIK inhibitor.

7. The method of claim 6, wherein the p55PIK inhibitor is present in the composition at a concentration of at least 0.1 wt. %.

8. The method of claim 1, wherein the composition reduces the expression level of p55PIK protein in ocular tissues.

9. The method of claim 1, wherein the composition increases tear secretion as measured by Schirmer test, and prolongs tear film break-up time as measured by fluorescein tear break-up time.

10. The method of claim 1, wherein the composition reduces corneal epithelial damage as measured by fluorescein staining.

* * * * *